United States Patent
McBride et al.

(10) Patent No.: US 8,100,092 B2
(45) Date of Patent: Jan. 24, 2012

(54) HYDROGEN SUPPLEMENTATION FUEL APPARATUS AND METHOD

(75) Inventors: Daniel McBride, Macomb, MI (US); Dominic Ciacelli, Macomb, MI (US)

(73) Assignee: Clean-Fuel Technologies, Inc., Macomb, MI (US)

(*) Notice: Subject to any disclaimer, the term of this patent is extended or adjusted under 35 U.S.C. 154(b) by 186 days.

(21) Appl. No.: 12/652,205

(22) Filed: Jan. 5, 2010

(65) Prior Publication Data

US 2010/0170454 A1   Jul. 8, 2010

Related U.S. Application Data

(60) Provisional application No. 61/142,456, filed on Jan. 5, 2009.

(51) Int. Cl.
*F02B 43/08* (2006.01)
(52) U.S. Cl. .................. 123/3; 123/DIG. 12
(58) Field of Classification Search ........ 123/3, DIG. 12
See application file for complete search history.

(56) References Cited

U.S. PATENT DOCUMENTS

| | | | |
|---|---|---|---|
| 3,648,668 A * | 3/1972 | Pacheco | 123/3 |
| 3,939,806 A * | 2/1976 | Bradley | 123/3 |
| 4,085,709 A * | 4/1978 | Tangri | 123/3 |
| 4,105,528 A | 8/1978 | Hasebe | |
| 4,107,008 A | 8/1978 | Horvath | |
| 4,271,793 A | 6/1981 | Valdespino | |
| 4,368,696 A | 1/1983 | Reinhardt | |
| 4,675,085 A | 6/1987 | Vasquez | |
| 5,183,565 A | 2/1993 | Zimmermann et al. | |
| 5,513,600 A * | 5/1996 | Teves | 123/3 |
| 6,209,493 B1 | 4/2001 | Ross | |
| 6,257,175 B1 | 7/2001 | Mosher et al. | |
| 6,336,430 B2 | 1/2002 | de Souza et al. | |
| 6,787,258 B2 * | 9/2004 | Prerad | 123/3 |
| 6,817,320 B2 | 11/2004 | Balan et al. | |
| 6,896,789 B2 | 5/2005 | Ross | |
| 7,021,249 B1 | 4/2006 | Christison | |
| 7,041,203 B2 | 5/2006 | Sullivan | |
| 7,143,722 B2 | 12/2006 | Ross | |
| 7,240,641 B2 | 7/2007 | Balan et al. | |
| 2001/0003276 A1 | 6/2001 | De Souza et al. | |
| 2004/0025807 A1 | 2/2004 | Jhetham | |
| 2004/0203166 A1 | 10/2004 | Sullivan | |
| 2005/0126515 A1 | 6/2005 | Balan et al. | |
| 2005/0252764 A1 | 11/2005 | Meller | |
| 2006/0131165 A1 | 6/2006 | Sullivan | |
| 2006/0179819 A1 | 8/2006 | Sullivan | |
| 2006/0179820 A1 | 8/2006 | Sullivan | |
| 2006/0251929 A1 | 11/2006 | Sullivan | |
| 2007/0045044 A1 | 3/2007 | Sullivan | |
| 2007/0074680 A1 | 4/2007 | Ross | |
| 2007/0107982 A1 | 5/2007 | Sullivan | |
| 2008/0088148 A1 | 4/2008 | Sullivan | |
| 2009/0320807 A1 * | 12/2009 | Cerny et al. | 123/527 |

FOREIGN PATENT DOCUMENTS

WO   2005/077058 A2   8/2005

* cited by examiner

*Primary Examiner* — Noah Kamen
(74) *Attorney, Agent, or Firm* — Young Basile

(57) ABSTRACT

A hydrogen supplementation fuel apparatus and method having a power source, a hydrogen generator and an accumulator for supplementing hydrogen gas to improve the fuel efficiency of internal combustion engines. The hydrogen generator uses electrodes that are helically wound about a separator to increase the hydrogen generation output.

20 Claims, 6 Drawing Sheets

HYDROGEN SUPPLEMENTATION FUEL APPARATUS AND METHOD

CROSS-REFERENCE TO RELATED APPLICATION

This application claims the benefit to U.S. Provisional Patent Application No. 61/142,456, filed Jan. 5, 2009, the entire contents of which is incorporated herein by reference.

TECHNICAL FIELD

The apparatus and method generally pertain to fuel supplementation systems and more specifically to hydrogen fuel supplementation systems.

BACKGROUND

There is increased interest and momentum in the United States and abroad to find alternatives to fossil or hydrocarbon-based fuels to reduce the dependency on oil. This interest in past years has been particularly acute in the field of internal combustion engines in passenger and commercial vehicles.

Prior devices have been proposed, for example, hybrid vehicles which combine use of gasoline and electric motors to supplement or reduce the amount of gasoline that is used. Prior systems have further proposed use of supplementing hydrogen along with gasoline to reduce gasoline consumption. These prior devices have suffered from many disadvantages which have limited the commercialization and acceptance in the marketplace.

There is a need to improve on prior alternative fuel or fuel supplementation systems which efficiently reduces consumption of traditional fuels, for example gasoline, and that is economical to manufacture, use and maintain. It is a further advantage if the fuel supplementation system is easy to integrate into existing internal combustion engines in vehicles already on the road to take advantage of an increase in fuel economy without having to make a large investment in acquiring a new vehicle having such advantages.

BRIEF SUMMARY

The present invention and method is a hydrogen fuel supplementation system for use with internal combustion engines, for example, passenger vehicles.

In one example of the invention, an on-board hydrogen generator using on-board generated electric power decomposes distilled water with an electrolyte through general electrolysis to generate hydrogen gas. The hydrogen gas is routed through an accumulator and into the intake manifold of the resident internal combustion engine in the vehicle.

In one example, the generator includes a dual fin separator inside the hydrogen generator which positions and separates four helically wound wire electrodes that selectively spiral through three sets of radially spaced openings in the separator producing three coaxially spaced coils or electrodes.

In another example, an accumulator is used to fill, store and supply water and electrolyte to the hydrogen generator and serves as a return reservoir for hydrogen gas produced by the generator prior to reaching the intake manifold. The accumulator further includes a baffle system to diminish movement of the stored fluid during dynamic motion of the vehicle.

In another example, a system controller is used which includes a timer relay circuit to delay initiation of the supplementation device based on the determined status of the vehicle, for example, on start up of a cold engine.

BRIEF DESCRIPTION OF THE DRAWINGS

The description herein makes reference to the accompanying drawings wherein like reference numerals refer to like parts throughout the several views, and wherein.

DETAILED DESCRIPTION

Examples of a hydrogen fuel supplementation device 10 and method of operation are shown in FIGS. 1-8. As shown in FIGS. 2-7, the hydrogen device 10 is shown in an exemplary application for use in a passenger automobile engine compartment to supplement the consumption of gasoline in a resident internal combustion engine (not shown) and increase fuel economy. As explained in detail below, the device and method may be used in other applications as known by those skilled in the art.

Figure 1:
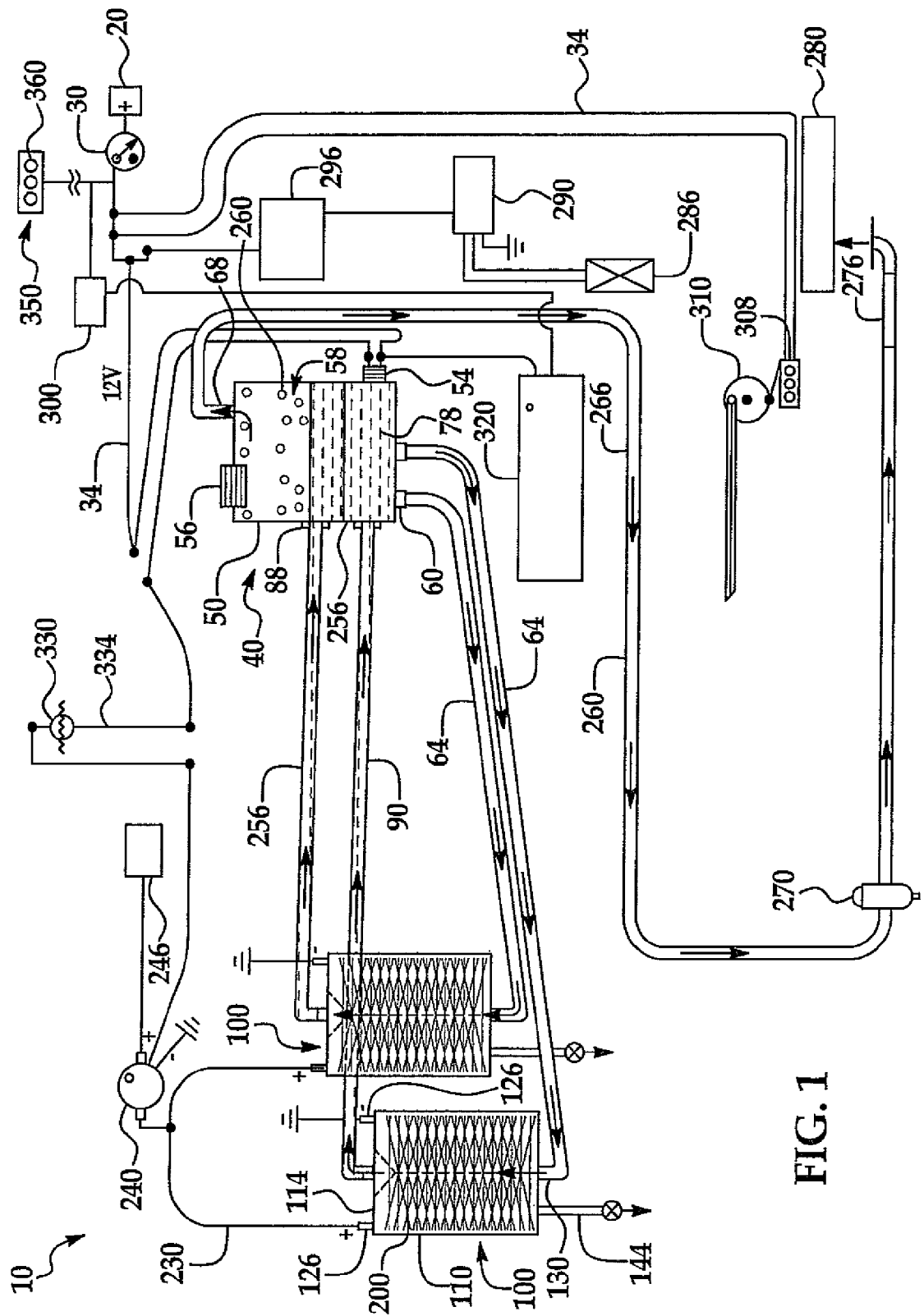
FIG. 1 is a schematic view of one example of the hydrogen fuel supplementation system.
Figure 2:
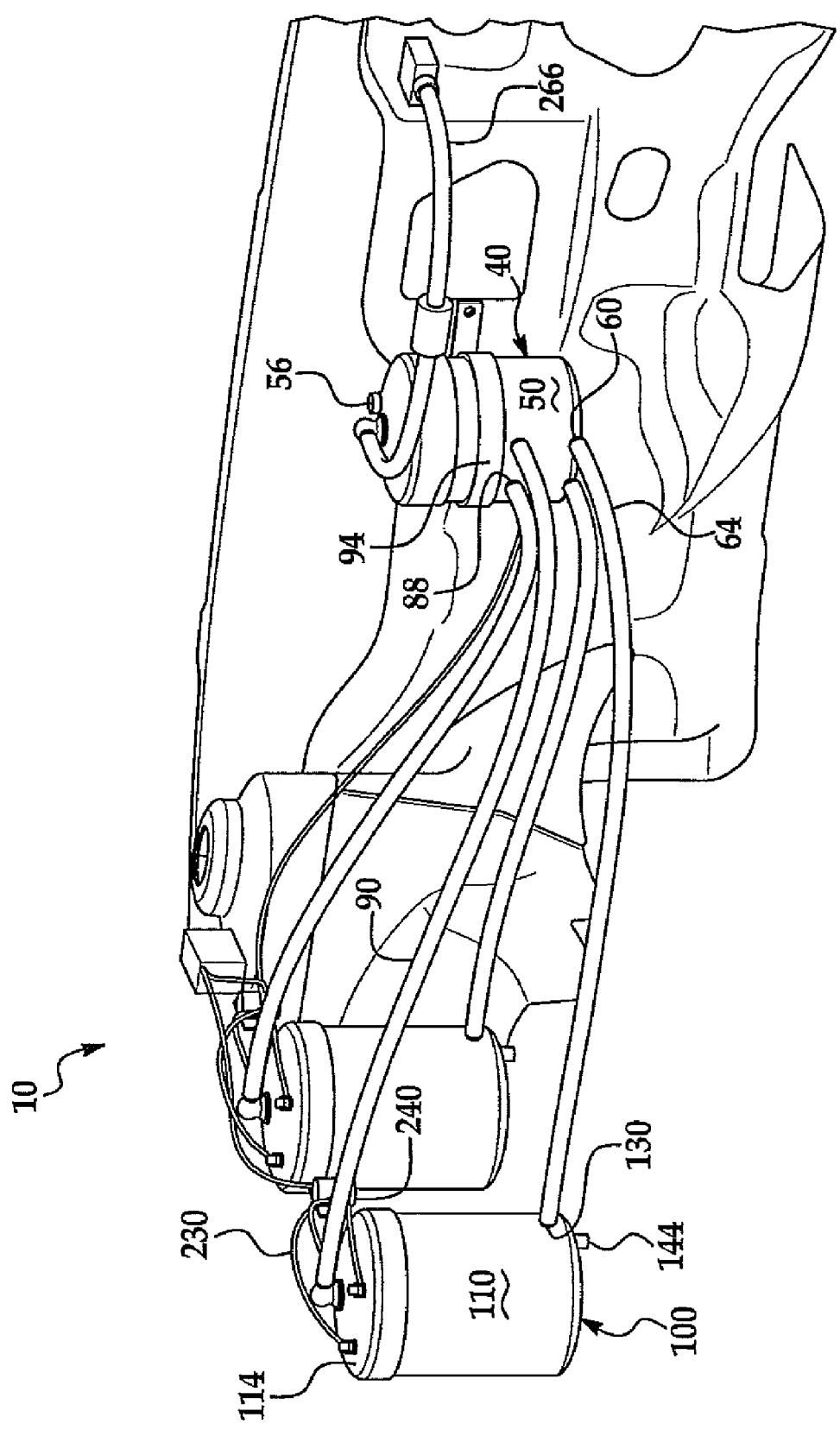
FIG. 2 is a partial perspective view of the example shown in FIG. 1 with an alternate example of an accumulator mounted in the engine compartment of a passenger vehicle.

Referring to FIGS. 1 and 2, an example of the device components, including optional components as described below, is generally shown. Referring specifically to FIG. 1, the device 10 includes an electrical power source 20. In use of device 10 in a passenger automobile, the source 20 is preferably in the form of an alternator or generator (not shown) which generates electricity for power supplied by the internal combustion engine. It is contemplated that other sources of power may be used, for example, the vehicle battery, or other sources of power and/or energy from the vehicle as known by those skilled in the art.

Device 10 further includes a manual on/off master switch 30 which preferably is positioned in the interior passenger compartment and activated by the driver. Switch 30 may take other forms such as push buttons or other actuation devices known by those skilled in the art. Although preferred as a manually operated switch, it is contemplated that other master on/off actuation devices that are not manually operated and rely on one or more signals from other vehicular systems may be used. In a preferred example, the device 10 will not be permitted to initiate operation or function if the internal combustion engine is not running.

As shown in FIG. 1, wires or other conductors 34 are used to transfer power from the power source 20 through other devices and sensors as explained in more detail below.

Figure 3:
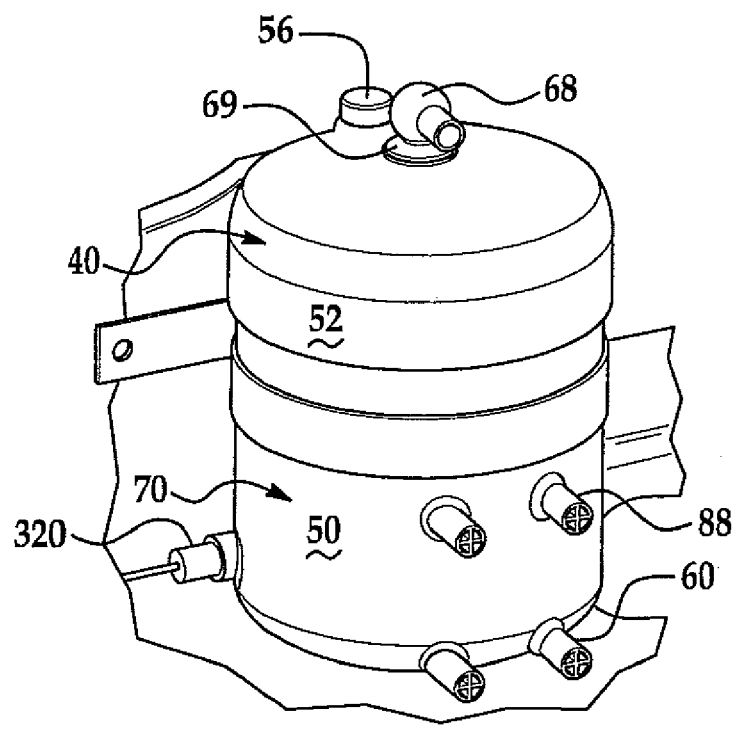
FIG. 3 is an enlarged perspective view of an example of an accumulator shown in FIG. 2.
Figure 4:
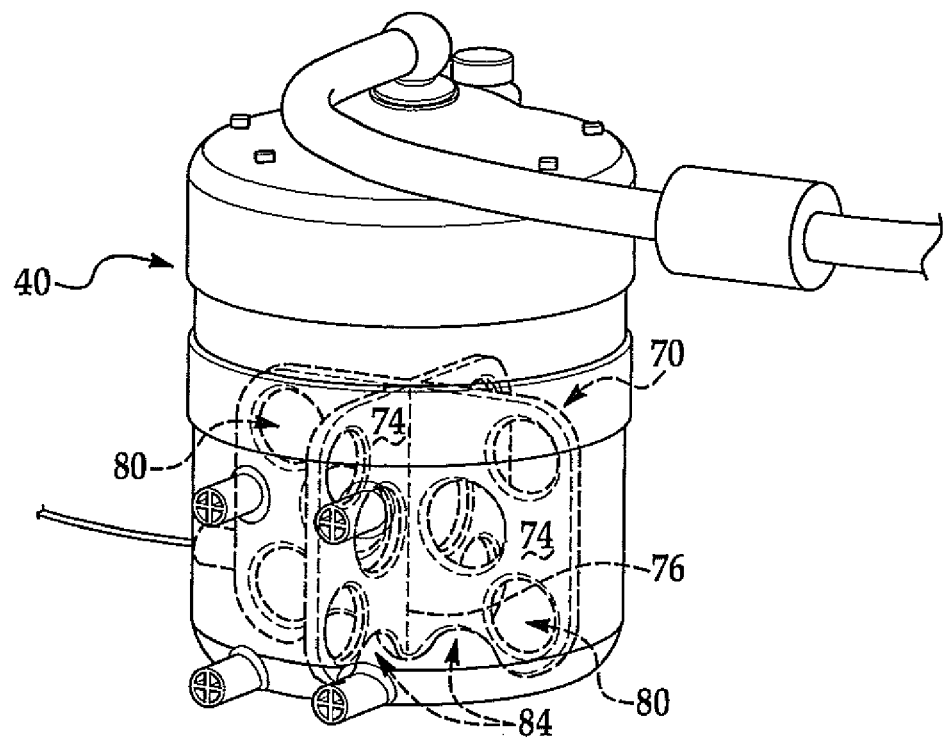
FIG. 4 is an enlarged perspective view of an example of an accumulator baffle.

Referring to FIGS. 1, 3 and 4, device 10 further preferably includes an accumulator 40 positioned in the engine compartment of a vehicle and is in electronic communication with the power source 20 through conductors 34 to terminals 54. In the example, accumulator 40 includes a housing 50 shown as generally having a cylindrical shape with a lid 52 which provides for an air-tight seal with housing 50. Housing 50 and lid 52 define an interior cavity 58. Accumulator 40 further includes a fill port 56 leading to cavity 58 and includes a closure cap (not shown) to provide a liquid and air-tight seal with lid 52. Cavity 58 is at least partially filed with a fluid 78, for example distilled water with an electrolyte as further described below. Accumulator housing 50 and lid 52 are preferably made from high temperature polymeric materials, but may be made from stainless steel, ferrous or other non-ferrous metals or other materials known by those skilled in the art. Accumulator 40 is preferably four to eight inches in diameter and six to twelve inches in height. Other sizes and materials known by those skilled in the art to suit the particular application may be used.

In the example shown in FIGS. 2 and 3, accumulator 40 further includes a fluid outlet port 60 (two shown) integral with housing 50. Fluid outlet ports 60 are reinforced with internal ribs providing a robust connection for a fluid fill tube 64 (two shown) which are further described below. Accumulator 40 further includes a return port 88 (two shown) similarly constructed as fluid outlet ports 60. Return tubes 90 are connected to ports 88 by use of hose clamps (not shown) or other tube securing fasteners or methods known by those skilled in the art. Alternate positions of fill tubes 64 and return tubes 90 are shown in FIG. 1. Other positions not illustrated may be used.

Accumulator 40 further includes a gas outlet connector 68 positioned at or near the top of lid 52. Connector 68 is in fluid communication with internal cavity 58. Connector 68 is secured to lid 52 through fasteners 69 forming a liquid and air-tight seal with lid 52. Connector 68 is preferably cast from brass although other materials may be used. Accumulator 40 further includes a connecting strap 94 to securely mount accumulator 40 to, for example, the sheet metal on the inside of an engine compartment.

Referring to FIG. 4, in one example, accumulator 40 includes a baffle 70 positioned inside cavity 58 for suppression of the dynamic movement of fluid positioned inside accumulator 40 as further described below. In one example of baffle 70, baffle 70 includes four sidewalls 74 extending vertically upward and connected at a central axis 76 as generally shown. Baffle 70 further includes one or more apertures 80 positioned in each side wall 74. Baffle 70 further includes notches 84 or other reliefs or cut-outs which are positioned to decrease or suppress the free flow of fluid inside cavity 58 as desired to suit the particular application. Other apertures or reliefs may be used as known by those skilled in the art. Baffle 70 is preferably connected to housing 50 through fasteners (not shown). Other methods of securing baffle 70 to housing 50, for example, being integrally molded into housing 50, using adhesive, ultrasonic welding, or other methods known by those skilled in the art. Baffle 70 is preferably made from the same material as housing 50 although other materials may be used. It is understood that baffle 70 may further take different forms from that shown to suit the particular application.

As shown in FIGS. 1, 2, 5 and 6, hydrogen device 10 further includes a generator 100 (two shown in FIG. 1) connected in electrical communication with power source 20 through conductors 34 and 230 and in fluid communication with accumulator 40 through fill tubes 64. Each generator 100 includes a housing 110 and a lid 114 defining an interior cavity 120. Generator lid 114 further includes conductive terminals 126 (four shown) extending vertically through the upper surface of the lid for electronic receipt of conductors 230 as generally shown. Conductors 230 are secured to terminals 126 by hex-head nuts threadingly engaged with terminals as generally shown. Housing 110 and lid 114 are preferably made from the same materials as the accumulator 40 although other materials known by those skilled in the art may be used. Generator 100 is preferably about six inches in diameter and approximately 10 inches in height so as to be packaged in the interior engine compartment with the resident engine. The generators 100 may be positioned in other areas of a passenger or commercial vehicle, for example, in the trunk or other storage area.

As shown in FIG. 1, accumulator 40 return ports 88 are preferably positioned in the engine compartment at a height greater than the top of the generators as further described below. Similarly, the accumulator fluid outlet ports 60 are preferably positioned at a height higher than the generator fluid intake ports as illustrated and described further below. As shown in FIG. 2, the accumulator may be positioned partially below the generators to suit the application and packaging area for device 10. In one example, a pump (not shown) may be used to force fluid 78 upward against gravity in the case where the accumulator is positioned partially below the generators.

Generators 100 further each include a fluid intake port 130 (one shown for each generator) for connection of fill tube 64 from accumulator 40. Intake port 130 is similarly constructed as outlet ports 60 on the accumulator. Generators 100 further include a outlet port 136 for the transfer of enriched fluid 256 discussed further below for return to accumulator 40 through return tube 90 (two shown). A return connector 140 in fluid communication with cavity 120 is sealingly attached to lid 114. In a preferred example, connector 140 is made from brass although other materials may be used. A drain 144 in fluid communication with interior cavity 120 is positioned on the bottom of housing 110. A cap (not shown) is used to close and seal drain 144.

Figure 5:
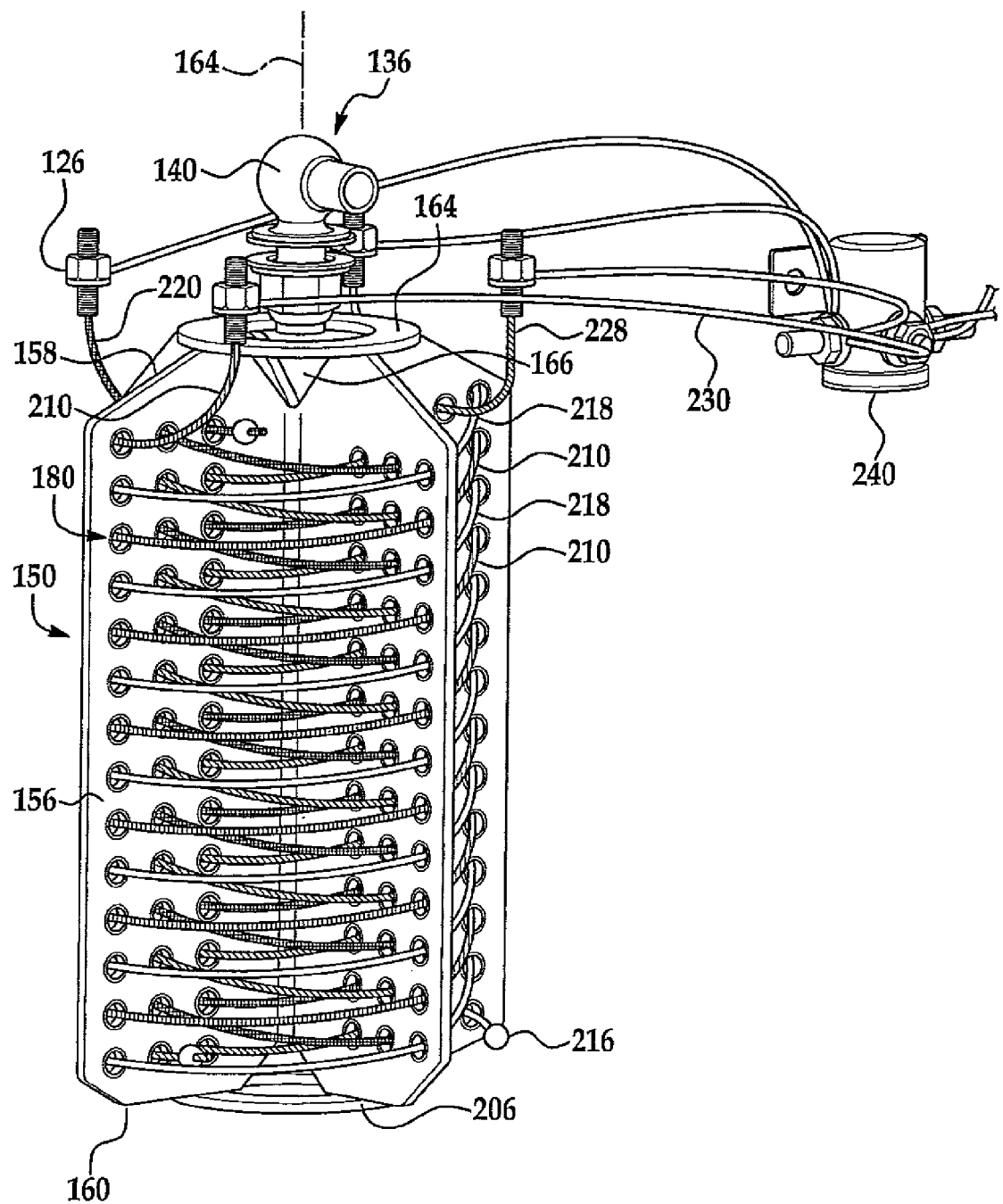
FIG. 5 is an enlarged perspective view of an example of the interior components of a hydrogen generator shown in FIG. 1.
Figure 6:
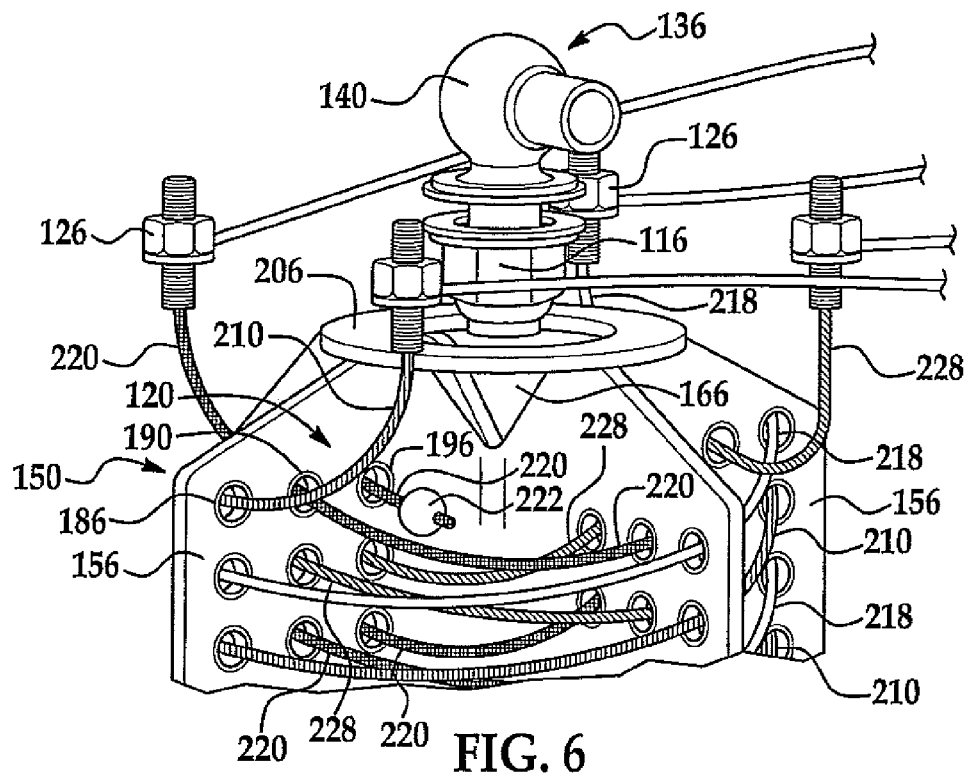
FIG. 6 is an enlarged, partial perspective view of the hydrogen generator shown in FIG. 5.

Referring to FIGS. 5 and 6, generator 100 includes a separator 150 positioned in interior cavity 120 in each generator 100. In one example, separator 150 includes four angularly spaced substantially planar fins 156 having a top portion 158 and a bottom portion 160. Fins 156 are connected together at an axis 164 as generally shown. In a preferred example, fins 156 are all integrally molded together. As shown, the connected fins 156 form a v-shaped notch 166 at the top and bottom of the separator. These v-notches 166 facilitate the accumulation, free flow and transfer of hydrogen gas toward the top of the generator. Each fin 156 includes a peripheral edge 170 radially extending outward from axis 164.

Separator 150 further includes a series of through apertures 180. In one example shown in FIG. 5, apertures 180 consist of three sets or series of radially spaced apertures through each fin including a first 186, second 190 and third 196 apertures of decreasing radial distance from axis 164. The first 186, second 190 and third 196 apertures further repeat and extend longitudinally along axis 164 spanning from the top 158 toward the bottom 160 as generally shown. In a preferred example, all first 186, second 190 and third 196 apertures have the same respective radial distance from axis 164 and have respective equal placement longitudinally along axis 164 as generally shown. It is contemplated that the respective apertures may vary in radial and longitudinal position to suit the particular application and power considerations without deviating from the present invention. Separator 150 is preferably made from non-conductive polymeric materials, for example lexan, acrylic or other high temperature polymers. Other non-conductive materials known by those skilled in the art may be used.

As best seen in FIG. 6, in a preferred example, each aperture 186, 190 and 196 includes a bushing 200 positioned around the interior circumference of each aperture. Bushing 200 is preferably made from high grade stainless steel but may be made from other materials known by those skilled in the art. Bushings 200 are preferably press fit into the apertures and are engaged through a frictional fit. Other methods of securing the bushings, including adhesive or other mechanical attachments, may be used.

In the example shown, separator 150 further includes connector rings 206 near the top and bottom of the fins 156 for increased structural stability of separator 150. Connector rings 206 may be made from the same materials as fins 156 and may be attached through adhesive or other mechanical fastening techniques known by those skilled in the art.

In one example shown in FIGS. 5 and 6, generator 100 further includes four electrodes or conductors. The ends of first electrode or conductor 210 and a second electrode 218 are positioned diametrically opposite one another across axis 164. As best seen in FIG. 5, at the bottom row of apertures 180, a first end is secured to a stop 216 which is larger in diameter than an inner diameter of bushing 200 (only the stop for first electrode 210 shown) preventing pull through of the end of the electrode. The first 210 and second 218 electrodes are then helically wound through only the first set of radial apertures 186 alternating every other aperture along axis 164 toward the top 158 of the separator 150. Each respective exposed end of the first 210 and second 218 electrode extending upward through the top of generator lid 114 is connected to oppositely charged positive and/or negative terminals 126 as generally shown. For example, first electrode 210 is connected to a positive terminal and second electrode 218 is connected to a negative terminal.

In the illustrated example in FIGS. 5 and 6, generator 100 further includes a third electrode 220 and a fourth electrode 228 the respective ends of which exiting separator 150 diametrically opposite similar to the first and second electrodes. In the example shown, each of third 220 and fourth 228 electrodes start at the third set of radial apertures 196 with a stop 222 as best seen if FIG. 6 (only stop 222 for third electrode 220 shown). In similar fashion to the first and second electrodes, only starting at the top of separator 150, third 220 and fourth 228 electrodes are helically wound in alternating fashion down through the third set of apertures 196 along axis 164 until the bottom most set of apertures are reached and then are wound upward along axis 164 back toward the top through the second set of radial apertures 190 as shown. Similarly, the respective ends of third 220 and fourth 228 electrodes connect to oppositely charged terminals. Alternate configurations and positions of the respective electrodes known by those skilled in the art may be used without deviating from the present invention.

It has been discovered that due to the spacing of first 186, second 190 and third 196 apertures, the length of the first 210 and second 218 electrodes is approximately the same length as the lengths of the third 220 and fourth 228 electrodes, in one example, each about seven (7) feet in total length. Other lengths and numbers of electrodes can be used to suit the particular application and required output as known by those skilled in the art. For example, as an alternative to four terminals 126 (two positive and two negative) as illustrated, two terminals may be used and both the positive and negative electrodes are commonly connected through the respective positive and negative terminals.

In a preferred example, each of the first 210, second 218, third 220 and fourth 228 electrodes are made from multi-strand high grade stainless steel cable. A preferred outer diameter 212 is approximately one-eighth (⅛) inch. Other conductive materials, diameters and configurations may be used as known by those skilled in the art.

Using the above construction of separator 150 and alternatingly positioned and charged first 210 and second 218 electrodes and the alternatingly positioned and charged third 220 and fourth 228 electrodes shown in FIGS. 5 and 6, it has been found that decomposition of fluid 78, further discussed below, and the resulting generation of hydrogen gas, is significantly increased over that of prior designs including, for example, traditional straight metal rod electrodes and plates. This is believed to be due, in part, to the present design's lower operating temperature of the fluid 78. The efficiency of the electrolysis process is reduced as the temperature of the fluid 78 approaches the boiling point.

Referring to FIGS. 1, 2, 5 and 6, the generators 100 terminals 126 are connected to electrical conductors 230 to a relay 240 which is connected by conductors 34 to the power source 20 and a fuse panel or block 246. In one example, relay 240 is an 80 amp continuous duty relay. A suitable relay is manufactured by Cole Hersey Marine. Other relays or equipment may be used to suit that particular application and required performance as known by those skilled in the art.

Figure 7:
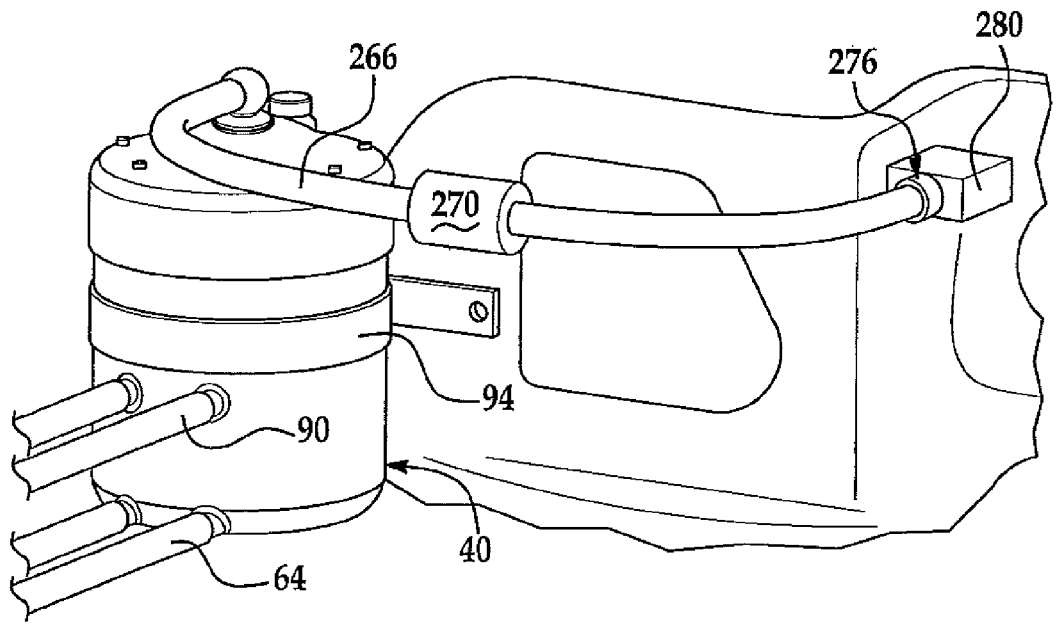
FIG. 7 is an perspective view of an alternate example of the accumulator shown in FIG. 2.

Referring to FIGS. 1, 2 and 7, generators 100 are in fluid communication with accumulator 40 through return tubes 90 as generally shown. As described, accumulator 40 includes a gas outlet connector 68 that is sealing connected to a gas transfer tube 266 which, in one example, leads to the air intake manifold connector 280 of an internal combustion engine (not shown). In the example illustrated in FIG. 1, a moisture separator 270 and a flame arrestor 276 is positioned along tube 266 between the accumulator 40 and manifold connector 280.

As further shown in FIG. 1, in a preferred example, device 10 is connected in electronic communication with a manifold absolute pressure sensor (MAP) 286 that is typically included with the resident internal combustion engine for monitoring the pressure inside the air intake manifold of the engine. The MAP sensor 286 allows monitoring of the amount of pressure, or vacuum, to assist in the regulation of fuel to air mixture that is entering the engine. The MAP sensor 286 is typically in electronic communication with an electronic fuel injection controller 290 which further assists in supply of the appropriate amount of fuel to the engine. These sensors and controllers, when placed in electronic communication with device 10, allow device 10, and the ultimate user to monitor and control the amount of supplemental hydrogen fuel that is supplied to the engine.

In a preferred example, device 10 includes a timer relay circuit 296 in electronic communication with an electronic fuel injector enhancer (EFIE) or controller 290 and MAP sensor 286 and device 10 system controller 300. Timer relay circuit 296 is used to selectively delay initiation of the device 10 production of supplemental hydrogen to the engine for a desired amount of time. It has been found that device 10 operates more effectively and efficiently when the vehicle engine is "warm," in other words, has been running for at least a short period of time. It has been found that a suitable delay of approximately eight (8) minutes from a cold start is preferred to initiate the generation of supplemental hydrogen. It is understood that the delay time may be preset or may be adjustable by the user, for example from about two (2) to twenty (20) minutes, to suit the particular engine or operating conditions As shown in FIG. 1, in one example, device 10 may further include an engine idle shut off-switch 308 in electronic communication with engine throttle control 310 as generally illustrated. Idle shut-off switch 308 may be used to suspend operation of generators 100 and/or supply of power thereto during times when the engine is at idle or remains at idle for a preprogrammed period of time through controller 300. This serves to reduce the power supply and consumption of power to generators 100 during selected periods to reduce the load on the engine's electrical system and thereby conserving consumption of gasoline thereby further increasing fuel economy.

As shown in FIGS. 1 and 3, in one example, device 10 may further include a high temperature sensor 320 positioned in thermal communication with accumulator 40 and in electronic communication with controller 300. In one example, if an undesired elevated temperature of accumulator 40 is reached, for example, a temperature exceeding 180 degrees Fahrenheit, sensor 320 would send a signal to controller 300 and operation of generators 100 and/or device 10 as a whole would be suspended or shut down.

As shown in FIG. 1, device 10 may further include an impact sensor 330 placed in electronic communication with conductor 34 leading to the relay 240, or optionally controller 300, to terminate operation of device 10 on a significant vehicular impact or acceleration due to a vehicular crash or other extraordinary event. Impact sensor can be in the form of an accelerometer or other sensor device known by those skilled in the art. It is understood that other sensors, switches and controls for operation and/or increased safety may be used without deviating from the present invention.

As shown in FIG. 1, device 10 may further include a user display panel and/or user interface 350 in electronic communication with controller 300 and/or directly to other monitoring devices in device 10 for example, timer relay circuit 296 and/or temperature sensor 320. User display panel 350 can include indicator lights 360 or other visual indicators, for example, dials, gages, liquid crystal display panel and other indicators known by those skilled in the art. User interface 350 is preferably positioned in the passenger compartment or other area visually accessible by an operator.

Figure 8:
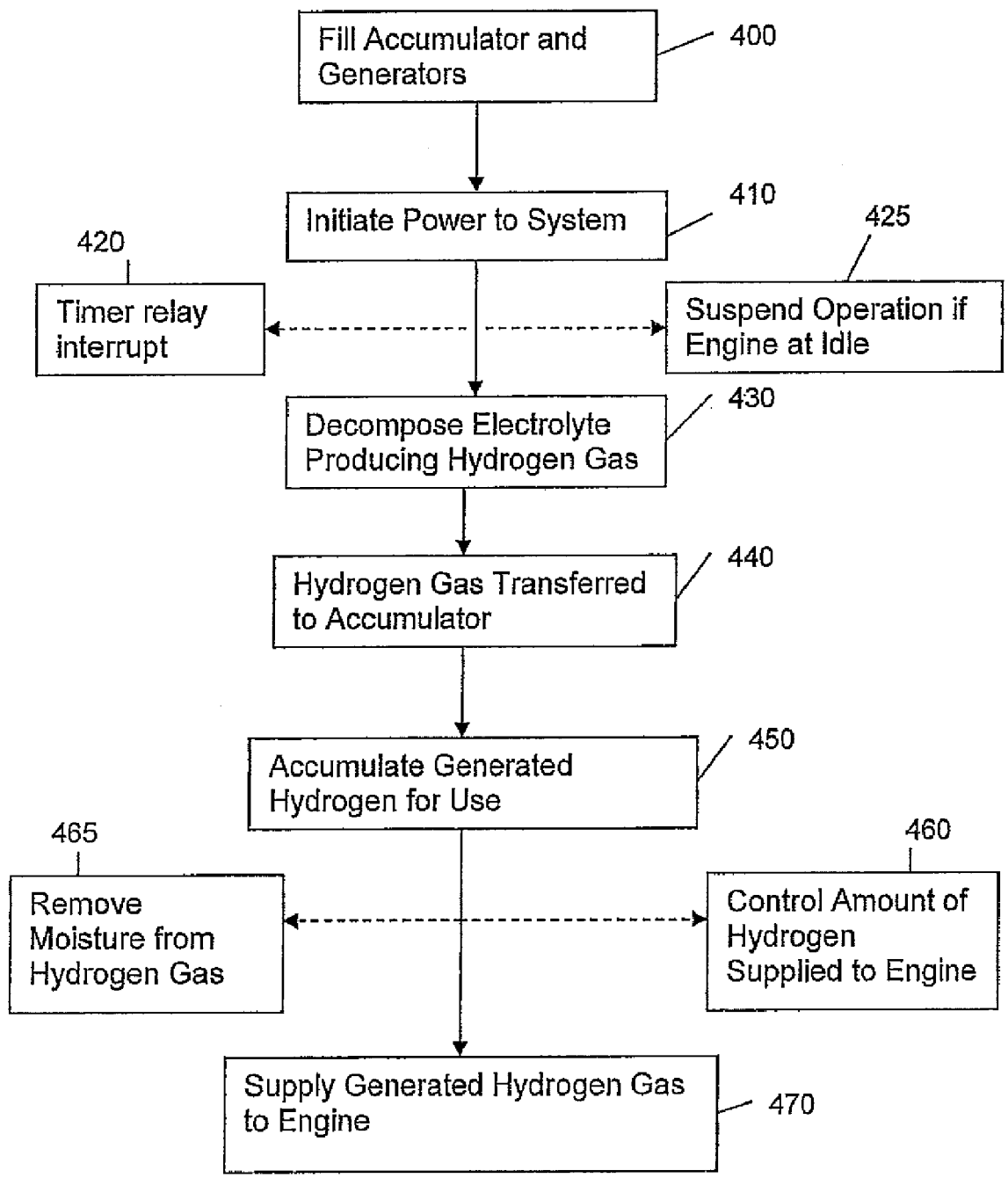
FIG. 8 is a flow chart of an example of a method of operation.

Referring to FIGS. 1 and 8, in an example of operation, device 10 is installed either as original equipment in a vehicle or other device in need of a supplemental hydrogen fuel supply or to an already constructed or resident vehicle as an aftermarket kit or assembly. Device 10's size and components lend itself for particularly useful application to existing passenger vehicles and can be installed by professional installers or potentially skilled end users.

In step 400, generators 100 are at least partially filled with fluid 78 through fill port 56 in accumulator 40. In one example, fluid 78 is demineralized water. In another example, fluid 78 includes an electrolyte of potassium hydroxide, sodium hydroxide or other suitable ionic compound. In a preferred example, sufficient fluid 78 is provided to almost or completely fill each generator 100 and partially fill accumulator to a level above return ports 88 as generally shown in FIG. 1. It has been determined that on normal usage, draining and replacement of fluid 78 in device 10 can be made approximately once a month.

In step 410, on a user manually activating device 10 through manipulation of master on/off switch 30, power provided from the electrical system of the vehicle, in one example the vehicle alternator (not shown), power is supplied through conductors 34 and 230 to the accumulator 40 and generators 100. In one example, controller 300 would initiate a system check of all sensors, for example, high temperature sensor 320, idle shut off switch 308 and impact sensor 330, prior to allowing power to be supplied through the conductors.

In one example step 420, although device 10 has been started and can draw power, timer relay circuit 296 starts an internal clock and interrupts power being transferred to the accumulator 40 and generators 100. In one example, timer relay circuit 296 interrupts the power supply for approximately 7 to 8 minutes, or other selected time period, while the engine normally runs and reaches a normal operating temperature.

In one example at step 425, if the engine is idle, or at other conditions known by those skilled in the art, temporary suspension of the operation of device 10 may occur through, for example, stopping the flow of power from the power source 20 to generators 100 by idle shut off switch 308. This reduces the power consumption by the device 10 when the engine demand is low. The temporary suspension ceases when the engine throttle 310 advances.

In step 430 the power supplied to the generators flows through the terminals 126 and is conducted by the first 210, second 218, third 220 and fourth 228 electrodes. This creates a magnetic field between oppositely charged electrodes, for example the first electrode 210 (typically serving as the positively charged cathode) and the second electrode 218 (typically serving as the negatively charged anode). A similar condition exists between the third 220 and fourth 228 electrodes. This field sends an electrical current through the fluid which decomposes the water molecules in the fluid by the process generally known as electrolysis producing gaseous hydrogen and oxygen inside generators 100. Each generator 100 is thereby converted into an electrolytic cell.

In step 440, the generated hydrogen and oxygen gas bubble to the top of housing 110 producing an enriched fluid 256 which passes through connector 140 and return tubes 90 back to accumulator 40. In one example, the accumulator 40 is positioned vertically above generators 100 so that fluid 78 flows by gravity to keep generators 100 filed with fluid 78. The generated hydrogen and oxygen gasses naturally flow back toward accumulator 40. In an alternate example, a pump (not shown) may be used to force the flow of fluid 78 and/or enriched fluid 256 to and from the accumulator and generator as needed.

In step 450, the generated hydrogen gas bubbles to the surface of fluid 78 stored in accumulator 40 and passes toward lid 52 and outlet connector 68.

In step 470, on demand from the load from the engine or other device being supplemented, the hydrogen gas is either naturally drawn, or may be forcibly transferred through transfer tube 266 toward intake manifold connector 280 or the throttle plate (not shown) for use by the engine.

In one example, in step 460, controller 300 controls the amount of hydrogen gas that is allowed to pass to the manifold connector 280 to supplement the gasoline simultaneously being provided the resident engine fuel supply. In one example, the amount of hydrogen gas supplied to the engine is approximately 40 percent of the total fuel being provided to the engine. It is understood that this percentage can range from 100 percent hydrogen supply to the engine or zero percent based on the conditions of the engine and desired fuel economy.

In one example, prior to supplying the hydrogen gas to the intake connector, a moisture removal step 465 may be employed as generally shown.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A hydrogen generation device for use in supplementing hydrogen fuel to an internal combustion engine, the device comprising:
   a power source;
   an accumulator in communication with the power source having an internal cavity for the storage of fluid;
   a hydrogen generator in electrical communication with the power source and in fluid communication with the accumulator, the generator having at least a first and a second electrode positioned in an internal cavity and separated from one another, wherein on supply of power to the electrodes, hydrogen gas is produced and is transferred to the accumulator; and
   the device further comprising at least one of
   (a) the generator further comprising a separator having a longitudinal axis and a plurality of longitudinally and radially spaced apertures about the axis, at least one of the first and the second electrodes is helically threaded through selected apertures around the axis, or
   (b) the accumulator cavity further comprising a hydrogen gas reservoir in communication with the generator and the internal combustion engine and a baffle positioned in the cavity in communication with the fluid to suppress dynamic movement of the fluid in the accumulator cavity.

2. The device of claim 1 wherein the first and the second electrodes are separately and alternatingly threaded through the selected apertures and helically wound about the separator axis.

3. The device of claim 1 wherein the first and the second electrodes are approximately the same linear length.

4. The device of claim 1 having the separator, wherein the separator further comprises two planar members intersecting at the axis forming four angularly spaced fins, each fin having the plurality of longitudinally and radially spaced apertures.

5. The device of claim 4 wherein the separator apertures comprise a first series, a second series and third series of apertures radially spaced from each other in concentric orientation about the axis and repeating longitudinally along the longitudinal axis.

6. The device of claim 5 further comprising a third and a fourth electrode, the third and fourth electrodes separately and alternatingly threaded though selected separator apertures and helically wound about the axis.

7. The device of claim 6 wherein the first and the second electrodes are exclusively and alternatingly threaded through the first series of apertures positioned radially furthest from the axis with respect to the second and the third series apertures, the third and the fourth electrodes are exclusively and alternatingly threaded through the second and the third series of apertures.

8. The device of claim 7 wherein the first, the second, the third and the fourth electrodes are about the same linear length.

9. The device of claim 1 having the hydrogen gas reservoir and baffle, the baffle further comprises two planar members intersecting at a longitudinal axis forming four angularly spaced fins, each fin having at least one aperture for controlled passage of fluid through the fin.

10. The device of claim 1 further comprising a controller in electronic communication with the power source, the generator and the accumulator for controlled generation and transfer of hydrogen gas between the generator and the internal combustion engine.

11. The device of claim 1 wherein the hydrogen generator comprises a plurality of hydrogen generators.

12. The device of claim 1 further comprising a temperature sensor in communication with the accumulator and the controller for monitoring at least one of the temperature of the fluid or the hydrogen gas in the accumulator.

13. The device of claim 1 further comprising an impact sensor in electrical communication between the power supply and the generator, the impact sensor operable to terminate the supply of power from the power source to the generator on a predetermined level of acceleration imparted to the device.

14. A hydrogen supplementation device for an internal combustion engine comprising:
    a power source;
    an accumulator having an internal cavity for housing a fluid and a baffle positioned in the fluid, the baffle having at least three angularly spaced fins each having an aperture for the controlled passage of fluid through the fin;
    a hydrogen generator in electrical communication with the power source and in fluid communication with the accumulator, the generator including a multi-fin separator and at least two electrodes, the at least two electrodes separately and alternatingly helically wound about a separator longitudinal axis; and
    a controller in electronic communication with the power source, the generator and the accumulator for controlled generation and distribution of hydrogen gas between the generator and the internal combustion engine.

15. The device of claim 14 wherein the generator separator further comprises a first series, a second series and a third series of apertures radially spaced from each other in concentric orientation about the axis and repeating longitudinally along the axis; and
    the at least two electrodes further comprising a third and a fourth electrode, wherein the first and the second electrodes are exclusively and alternatingly threaded through the first series of apertures positioned radially furthest from the axis with respect to the second and third series of apertures, the third and the fourth electrodes are exclusively and alternatingly threaded through the second and the third series of apertures.

16. A method for supplementing hydrogen gas fuel for use in an internal combustion engine, the method comprising:
    generating a source of electrical power;
    supplying a fluid and the source of electrical power to a hydrogen generator;
    conducting the electrical power through at least two electrodes separatingly and alternatingly helically wound about a separator having a longitudinal axis positioned in the generator;
    decomposing the fluid to produce hydrogen gas; and
    transferring the hydrogen gas to the internal combustion engine.

17. The method of claim 16 further comprising the step of transferring the generated hydrogen gas to an accumulator positioned between the generator and the internal combustion engine.

18. The method of claim 17 further comprising the step of temporarily storing the generated hydrogen gas in a reservoir defined by the accumulator.

19. The method of claim 16 further comprising the step of suspending generation of hydrogen gas while the internal combustion engine is at idle operation.

20. The method of claim 16 further comprising the step of selectively controlling the amount of generated hydrogen transferred to the internal combustion engine.

* * * * *